US00PP26841P3

(12) United States Plant Patent
Verhoef

(10) Patent No.: US PP26,841 P3
(45) Date of Patent: Jun. 21, 2016

(54) *WEIGELA* PLANT NAMED 'SLINGCO 2'

(50) Latin Name: *Weigela hybrida*
Varietal Denomination: Slingco 2

(71) Applicant: Gijsbertus Verhoef, Hazerswoude (NL)

(72) Inventor: Gijsbertus Verhoef, Hazerswoude (NL)

( * ) Notice: Subject to any disclaimer, the term of this patent is extended or adjusted under 35 U.S.C. 154(b) by 64 days.

(21) Appl. No.: 14/121,958

(22) Filed: Nov. 7, 2014

(65) Prior Publication Data

US 2016/0135346 P1 May 12, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para

(57) ABSTRACT

A new cultivar of *Weigela* plant named 'Slingco 2' that is characterized by a compact habit, green foliage, red flowers and continuous flowering from summer to autumn.

1 Drawing Sheet

Botanical classification: *Weigela hybrida.*
Variety denomination: 'Slingco 2'.

BACKGROUND OF THE INVENTION

The present invention relates to a new and distinct cultivar of *Weigela* plant botanically known as *Weigela hybrida* and hereinafter referred to by the cultivar name 'Slingco 2'.

The new cultivar is the product of a breeding program conducted by the inventor in a cultivated area of Hazerswoude, The Netherlands. The objective of the breeding program was to develop new *Weigela* cultivars with attractive red flowers.

'Slingco 2' originated from open pollination of the female or seed parent *Weigela* 'Red Prince' (not patented) in 2008. The male or pollen parent plant is unknown. The cultivar 'Slingco 2' was selected by the inventor in 2010 as a single plant within the progeny of the stated cross in a cultivated area of Hazerswoude, The Netherlands.

Asexual reproduction by softwood cuttings of the new cultivar 'Slingco 2' was first performed in 2010 in Hazerswoude, The Netherlands. Since that time, under careful observation, the unique characteristics of the new *Weigela* cultivar have been uniform, stable and reproduced true to type in successive generations of asexual reproduction.

SUMMARY OF THE INVENTION

The following represent the distinguishing characteristics of the new *Weigela* cultivar 'Slingco 2'. These traits in combination distinguish 'Slingco 2' as a new and distinct cultivar apart from other existing varieties of *Weigela* known to the inventor. 'Slingco 2' has not been tested under all possible conditions and phenotypic differences may be observed with variations in environmental, climatic, and cultural conditions, however, without any variance in genotype.

1. *Weigela* 'Slingco 2' exhibits a compact habit.
2. *Weigela* 'Slingco 2' exhibits red flowers.
3. *Weigela* 'Slingco 2' exhibits continuous flowering from summer to autumn.
4. *Weigela* 'Slingco 2' exhibits green foliage.

The closest comparison plant is the female parent plant *Weigela* 'Red Prince'. The new cultivar 'Slingco 2' is distinguishable from 'Red Prince' in the following characteristics:

1. *Weigela* 'Slingco 2' exhibits a more compact habit and a shorter overall height than 'Red Prince'.
2. *Weigela* 'Slingco 2' exhibits a large number of dark red flowers. In contrast, the flowers of 'Red Prince' are purple red and are smaller in number.
3. *Weigela* 'Slingco 2' exhibits continuous flowing from summer to autumn. In contrast, the flowers of 'Red Prince' do not continuously flower.

The new cultivar *Weigela* 'Slingco 2' can be compared to *Weigela* 'Verweig 6' (not patented). The new cultivar 'Slingco 2' is distinguishable from 'Verweig 6' in the following characteristics:

1. *Weigela* 'Slingco 2' exhibits dark red flowers. The flowers of 'Verweig 6' are purple red.

BRIEF DESCRIPTION OF THE DRAWING

The accompanying photograph illustrates the distinguishing traits of *Weigela* 'Slingco 2'. The plant in the photograph shows an overall view of a three year old outdoor field grown plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Weigela* cultivar named 'Slingco 2'. Data was collected in Hazerswoude, The Netherlands from three year old outdoor field grown plants. The time of year was June and the temperatures ranged from 12-28° Centigrade during the day and 8-15° Centigrade during the night. The light level was natural outdoor light and there were no photoperiodic treatments or growth retardants used. Color determinations are in accordance with The Royal Horticultural Society Colour Chart, $5^{th}$ edition 2007, except where general color terms of ordinary dictionary significance are used. The growing requirements are similar to the species.

Botanical classification: *Weigela hybrida* 'Slingco 2'.

Parentage: 'Slingco 2' resulted from open pollination of the female or seed parent *Weigela* 'Red Prince'.

Annual or perennial: Perennial.

Plant type: Shrub.

Suitable container size: 1.5 liter and larger.

Plant shape: Flattened globe shaped.

Growth habit: Broad upright, free branching.

Height: Average 125.0 cm. in height.

Width: Average 145.0 cm. in diameter.

Vigor: Moderate.

Growth rate: In spring approximately 10 cm. per month.

Low temperature tolerance: USDA Zone 5.

High temperature tolerance: 35 degrees Centigrade.

Propagation: Softwood cuttings.

Time to initiate roots: 21 to 28 days are required to initiate roots at 18 degrees Centigrade in the summer.

Time to produce a rooted plant: 60 days are required to produce a rooted plant at 16-22 degrees Centigrade in the summer.

Crop time: Approximately 18 months are required to achieve a finished plant from cuttings.

Root system: Main roots moderately thick, other roots moderately fine.

Stem:

*Branching habit*.—Free branching.

*Basal branching*.—Yes.

*Average number of lateral branches*.—70.

*Pinching*.—Not required, pinching will improve branching.

*Lateral branch diameter*.—Average 7 mm. in diameter.

*Lateral branch length*.—Average 79.9 cm. in length.

*Internode length*.—Approximately 5.9 cm. between nodes.

*Stem appearance*.—Slightly quadrangular in shape, moderately glossy, older branches rounded.

*Stem aspect*.—Upright to outward with an average angle 30 degrees from vertical.

*Stem strength*.—Moderate.

*Stem color immature*.—145A.

*Stem color mature*.—175B turning 199B on older stems.

*Pubescence*.—Upper internodes of young shoots covered with soft short hairs, average 0.25 mm. in length, 157D in color.

Foliage:

*Leaf arrangement*.—Opposite.

*Compound or single*.—Single.

*Quantity of leaves per lateral branch*.—Average 28.

*Leaf shape*.—Ovate.

*Leaf tip*.—Apiculate.

*Leaf base*.—Obtuse.

*Leaf margin*.—Finely serrate.

*Leaf dimensions*.—Length 12.6 cm; width 7.2 cm.

*Leaf texture* (*both sides*).—Slightly glossy.

*Pubescence*.—Main vein on both sides sparsely covered with short hairs, 0.25 mm. in length, color 157D.

*Vein pattern*.—Pinnate.

*Leaf color young, upper surface*.—166A.

*Leaf color young, lower surface*.—165A.

*Leaf color mature, upper surface*.—N137C.

*Leaf color mature, lower surface*.—146B.

*Vein color, upper side*.—146B.

*Vein color, under side*.—147D.

*Leaf attachment*.—Petiolate.

*Petiole dimensions*.—8.5 mm. in length; 3.5 mm. in width; 3.0 mm. in height.

*Petiole color*.—146C.

*Durability of foliage to stress*.—High.

Flower:

*Flower arrangement*.—Solitary, in pairs or in clusters, terminal and in leaf axils.

*Inflorescence type*.—Solitary in pairs or in clusters.

*Flower type*.—Single, campanulate.

*Flowering habit*.—Once per year.

*Natural flowering season*.—Spring to autumn.

*Time to flower from planting*.—Approximately 8 months.

*Quantity of flowers per lateral stem*.—Average 40.

*Quantity of flower buds per lateral stem*.—Average 100.

*Quantity of flowers and buds per plant*.—Average 10,000.

*Rate of flower opening*.—Approximately 75% of flowers are open at one stage.

*Fragrance*.—None.

*Bud length*.—Average 1.7 cm.

*Bud diameter*.—Average 5 mm. in diameter.

*Bud shape*.—Narrow obovate.

*Rate of opening*.—Approximately 7 days.

*Bud color*.—53A; base 46A.

*Flower aspect*.—Outward to upright.

*Flower shape*.—Campanulate.

*Flower dimensions*.—Average 2.0 cm. in diameter and 3.2 cm. in height.

*Flower longevity*.—Approximately 12 days.

*Persistent or self-cleaning*.—Self-cleaning.

*Number of petals*.—Five in number.

*Petal arrangement*.—Rotate, fused into a trumpet shaped corolla.

*Petal appearance*.—Dull.

*Petal texture*.—Smooth.

*Petals fused*.—Yes, lower 70% fused.

*Petal shape*.—Spathulate.

*Petal margin*.—Entire.

*Petal apex*.—Obtuse.

*Petal dimensions*.—Average 3.2 cm. in length and free part 0.9 mm. in width.

*Petal color when opening* (*upper side*).—Between 53A and 185A; base 53A.

*Petal color when opening* (*under side*).—Between 53A and 185A; base 53A.

*Petal color fully opened* (*upper side*).—46A.

*Petal color fully opened* (*under side*).—46A.

*Petal color fading to*.—185A.

Sepals:

*Number of sepals*.—Average 5.

*Sepal arrangement*.—Rotate, lower 25% fused.

*Sepal texture*.—Smooth; dull both surfaces; sparsely covered with short hairs; 0.2 mm in length; color 155A.

*Sepal shape*.—Linear.

*Sepal margin*.—Entire.

*Sepal apex*.—Narrow acute.

*Sepal base*.—Narrow cuneate.

*Sepal dimensions*.—Average 12 mm. in length and 1.5 mm. in width.

*Sepal color, young* (*upper side*).—144C with tinges of 178B.

*Sepal color, young* (*under side*).—150B with tinges of 178A.
*Sepal color, mature* (*upper side*).—150B with tinges of 178B.
*Sepal color, mature* (*under side*).—150B with tinges of 180A.

Calyx:
*Calyx shape*.—Rotate.
*Calyx dimensions*.—Average 12 mm. in length and 7 mm. in diameter.

Pedicels:
*Pedicel dimensions*.—Average 12 mm. in length and 1 mm. in diameter.
*Pedicel angle*.—35° from vertical.
*Pedicel strength*.—Moderately strong.
*Pedicel color*.—175B to 178D.

Reproductive organs:
*Stamen number*.—Average 5.
*Anther shape*.—Dorsifixed, narrow oblong, filaments implanted in petals.
*Anther length*.—4 mm.
*Anther color*.—186B.
*Filament length*.—10 mm.
*Filament color*.—53B.
*Amount of pollen*.—Moderate.
*Pollen color*.—158D.
*Number of pistils*.—Average 1.
*Pistil length*.—3.2 cm.
*Stigma shape*.—Club shaped.
*Stigma color*.—157C.
*Style length*.—3.0 cm.
*Style color*.—157D.
*Ovary color*.—175B.

Fruit and seed production: Fruit and seed development has not been observed to date.

Disease and pest resistance: Disease and pest resistance has not been observed to date.

The invention claimed is:

1. A new and distinct variety of *Weigela* plant named 'Slingco 2' as described and illustrated.

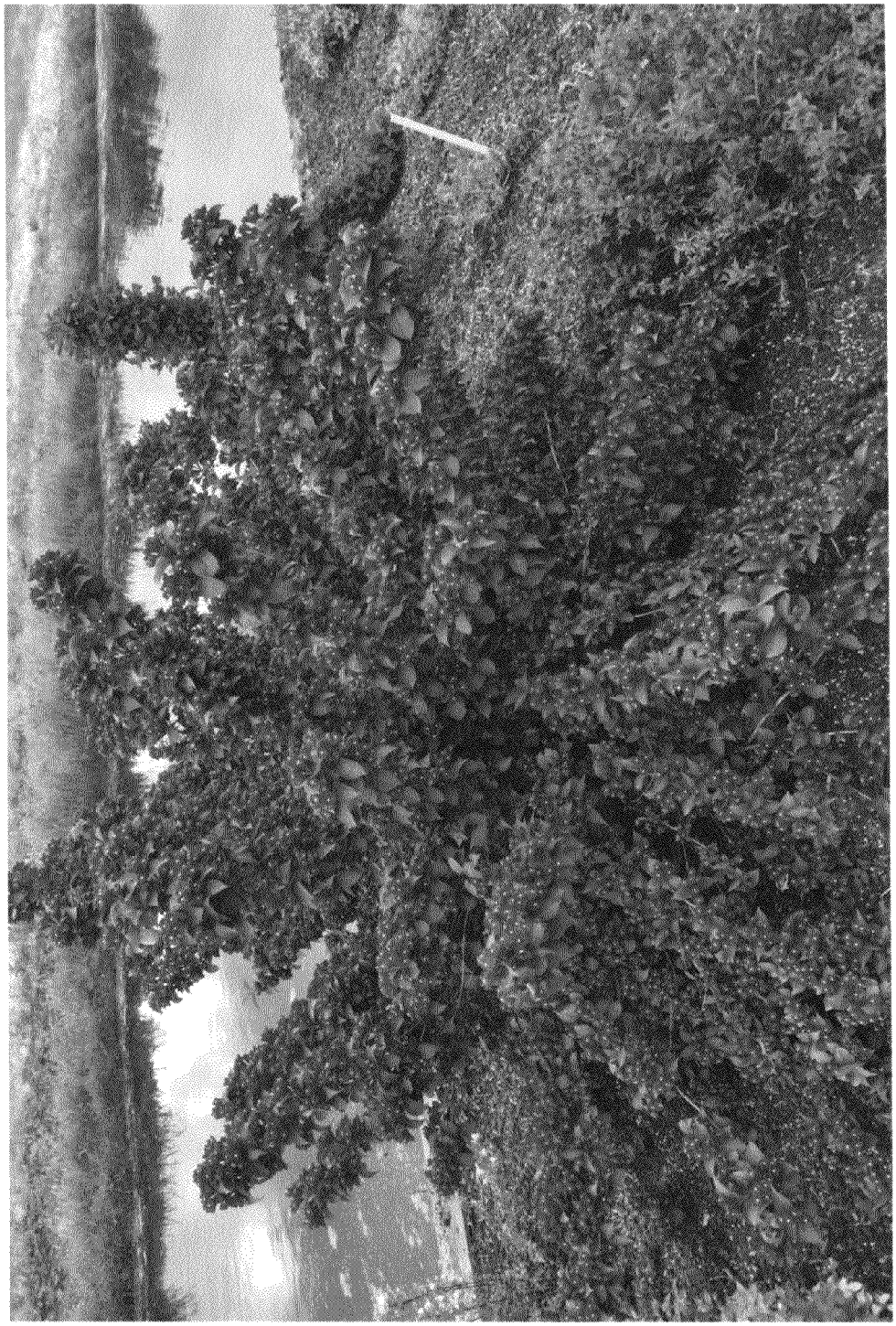

* * * * *